(12) United States Patent
Palumbo et al.

(10) Patent No.: US 6,350,256 B1
(45) Date of Patent: Feb. 26, 2002

(54) SHAPED SKIN ATTACHMENT MEANS FOR A FAECAL COLLECTOR

(75) Inventors: Gianfranco Palumbo, Bad Homburg; Vincenzo D'Acchioli, Kelkheim am Taunus, both of (DE)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/445,939

(22) PCT Filed: Jun. 26, 1998

(86) PCT No.: PCT/US98/13357

§ 371 Date: Dec. 20, 1999

§ 102(e) Date: Dec. 20, 1999

(87) PCT Pub. No.: WO99/00084

PCT Pub. Date: Jan. 7, 1999

(30) Foreign Application Priority Data

Jun. 28, 1997 (EP) .............................................. 97110602
Jun. 28, 1997 (EP) .............................................. 97110603
Jun. 28, 1997 (EP) .............................................. 97110604

(51) Int. Cl.$^7$ ........................... A61F 5/445; A61F 5/448
(52) U.S. Cl. ....................... 604/339; 604/327; 604/331; 604/337; 604/338; 604/355
(58) Field of Search ................................ 604/327, 331, 604/337, 338, 339, 341, 342, 348, 355, 385.19

(56) References Cited

U.S. PATENT DOCUMENTS

| 3,577,989 A | | 5/1971 | Anderson ..................... 128/283 |
| 3,804,093 A | * | 4/1974 | Fell ............................. 128/286 |
| 4,968,312 A | * | 11/1990 | Kahn ....................... 604/388.1 |
| 6,168,583 B1 | * | 1/2001 | Tanji et al. ............. 604/385.14 |
| 6,168,584 B1 | * | 1/2001 | Allen et al. ............. 604/385.19 |

FOREIGN PATENT DOCUMENTS

| EP | A 0 245 064 | * 11/1987 | ............. A61F/5/44 |
| EP | 0 753 290 A | 1/1997 | |
| GB | 1 092 274 A | 11/1967 | |
| GB | 2 116 849 A | 10/1983 | |
| JP | 08 117261 | 5/1996 | |

* cited by examiner

Primary Examiner—John G. Weiss
Assistant Examiner—Michael Bogart
(74) Attorney, Agent, or Firm—Leonard W. Lewis; Larry L. Huston; Jeffrey R. Moore

(57) ABSTRACT

A device for collecting body waste. The device has a bag with an aperture to allow entry of body waste. A flange permits the device to be attached to the body of a wearer. Upstanding from the flange is a projection for sealing against the body of the wearer. The projection is resiliently deformable to promote comfort and better sealing.

7 Claims, 3 Drawing Sheets

SHAPED SKIN ATTACHMENT MEANS FOR A FAECAL COLLECTOR

FIELD OF THE INVENTION

The present invention relates to a body fitting faecal management device. In particular, the present invention is directed towards faecal management devices with improved skin attachment means such that improved body fit and a tight seal is provided between the body of the wearer and the skin, thereby preventing contact between the faecal material and the urinary tract. The devices find particular utility for female wearers of such devices.

BACKGROUND OF THE INVENTION

Faecal management devices are known articles of manufacture that are designed to be worn principally by incontinence sufferers and infants. Such faecal management devices are attached to the anal region of the wearer and are intended to entrap and immediately contain faecal material and other bodily discharges. As a consequence, these devices are functionally effective in eliminating the problem of smearing on the skin of the wearer; in lessening epidermal irritation; in preventing contamination of articles such as clothing and bedding; and even in preventing the soiling of the carers themselves. Nevertheless, a problem often encountered during the use of such faecal management devices is that some of the faecal material can flow towards the urinary tract of the wearer in particular for female wearers into the sensitive urethra of the wearer. Typically, the presence of such faecal material can lead to a nasty infections in this area. Such a condition is most undesirable, painful and distressing to the bedridden wearer or to the infant.

Many articles exist on the market that allege the entrapment and immediate containment of faecal material in an effective manner. The prior art is rich with such examples. For instance, WO 96/19167 describes an absorbent article adapted to contain faecal material and highly fluidic material that is expelled at high velocity. The absorbent article comprises faecal containment members positioned transversely outward of the absorbent assembly, which function by interrupting the lateral movement of the faecal material. The faecal containment members are formed of resilient and porous materials to maintain and provide sufficient void volume to collect the faecal material, respectively. WO 94/14395 discloses a disposable absorbent article comprising a transverse partition disposed on the body facing surface of the topsheet and extending outwardly therefrom, to be upstanding and extend away from the plane of the disposable absorbent article. The transverse partition divides the absorbent article into a front portion and a rear portion, and presents an abrupt discontinuity between the two portions. Faecal material deposited in the rear portion is obstructed from longitudinally migrating to the front portion by the transverse partition. WO 97/01316 details a diaper with a bag for collecting faecal material and a urine collector for storing urine. The bag is formed by doubling over the diaper along a central imaginary line (perpendicular to the longitudinal sides of the diaper) and by drawing the edges (spaced apart from the central imaginary line) parallel to the imaginary line together. In such a manner, the faecal material is isolated from the skin of the wearer.

Japanese application JP 08-117 261 A discloses a diaper having a bag like structure, which is designed for incontinence sufferers. The bag comprises a slit or a hole in a position facing the anus with the slit or hole being surrounded by a surface coated with adhesive. The bag is formed of a water-repellent material. U.S. Pat. No. 3 577 989 details a disposable plastic elimination-rapping bag for incontinence sufferers. The flange is specifically designed and shaped such that it is generally convex at its curved rearward end while being generally concave at its forward end. In particular, for a female patient, the convex portion of the flange is adapted to closely follow the curved body contour and to fit between the cheeks of the buttocks and below and around the anus while the concave forward end portion of the flange is designed to closely follow the curved contour of the body of the patient above the vulva. Between the end portions of the flange are elongated side portions dimensioned to closely follow the curved body contour between the anus, cheeks and upper legs of the sufferer. EP 0 245 064 describes a faecal incontinence bag having flexible front and rear walls secured together around their periphery. The front wall has a hole for entry of the matter discharged by the wearer. The hole is surrounded by an adhesive pad of skincompatible water-resistant material secured to the external surface of the front wall. The pad is generally heart-shaped so that when in position the concave portion of the heart-shaped pad is towards the front of the wearer. For all the prior art cases, the faecal matter is not entirely contained in the bag of the faecal management device. It is known that some of the faecal material seeps forward from the anal region and creeps into the urethra.

Nonetheless, the need exists for a faecal management device that is extremely effective in completely isolating the faecal material from the sensitive urinary tract of the wearer. The present invention addresses this need by providing a projection at the front portion of the flange. It has been found that the presence of such a projection is uniquely advantageous and prevents the flow of faecal material out of the front portion of the flange towards the urinary tract. Furthermore, the presence of such a projection on the faecal management device causes no discomfort to the wearer, leads to a great reduction in infections and epidermal irritations derived from faecal material and results in a high level of wearer and carer satisfaction in relation to skin healthiness.

In another aspect of the present invention, the faecal management device with this projection can be advantageously used with a disposable diaper. The prior art is silent on such a combination. As described above, none of the prior art documents discloses two separate entities that work synergetically to isolate the faecal material from the sensitive organs of the wearer and which furthermore isolate the skin of the wearer from the absorbent material of the diaper.

SUMMARY OF THE INVENTION

A faecal management device constructed in accordance with the present invention comprises a bag having an aperture and an anatomically-shaped flange surrounding the aperture for adhesive attachment to the perianal area of the wearer. The anatomically-shaped flange is attached to the bag and comprises an outer periphery, an inner periphery adjacent to the aperture, a longitudinal centerline and a transverse centerline wherein the transverse centerline segments the flange into a front portion and a rear portion.

In particular, the flange comprises a projection in the front portion. The projection is disposed between the outer periphery and the inner periphery of the flange in a direction parallel to the longitudinal direction. Preferably, the projection extends from the outer periphery to the inner periphery and is disposed in a symmetrical manner. The projection has an effective height ranging from 0.5 millimeters to 15 millimeters, preferably from 2 millimeters to 10 millimeters, more preferably an effective height of about 3 to 7 millimeters. The projection is particularly beneficial for female wearers where the projection is are adapted to fit snugly between the vulva and the anus, i.e., the perineum of the female wearer.

In another aspect of the present invention, the present faecal management device is used in combination with a disposable diaper.

BRIEF DESCRIPTION OF THE DRAWINGS

It is believed that the invention will be better understood from the foregoing description in conjunction with the accompanying drawings in which.

DETAILED DESCRIPTION OF THE INVENTION

Figure 1:
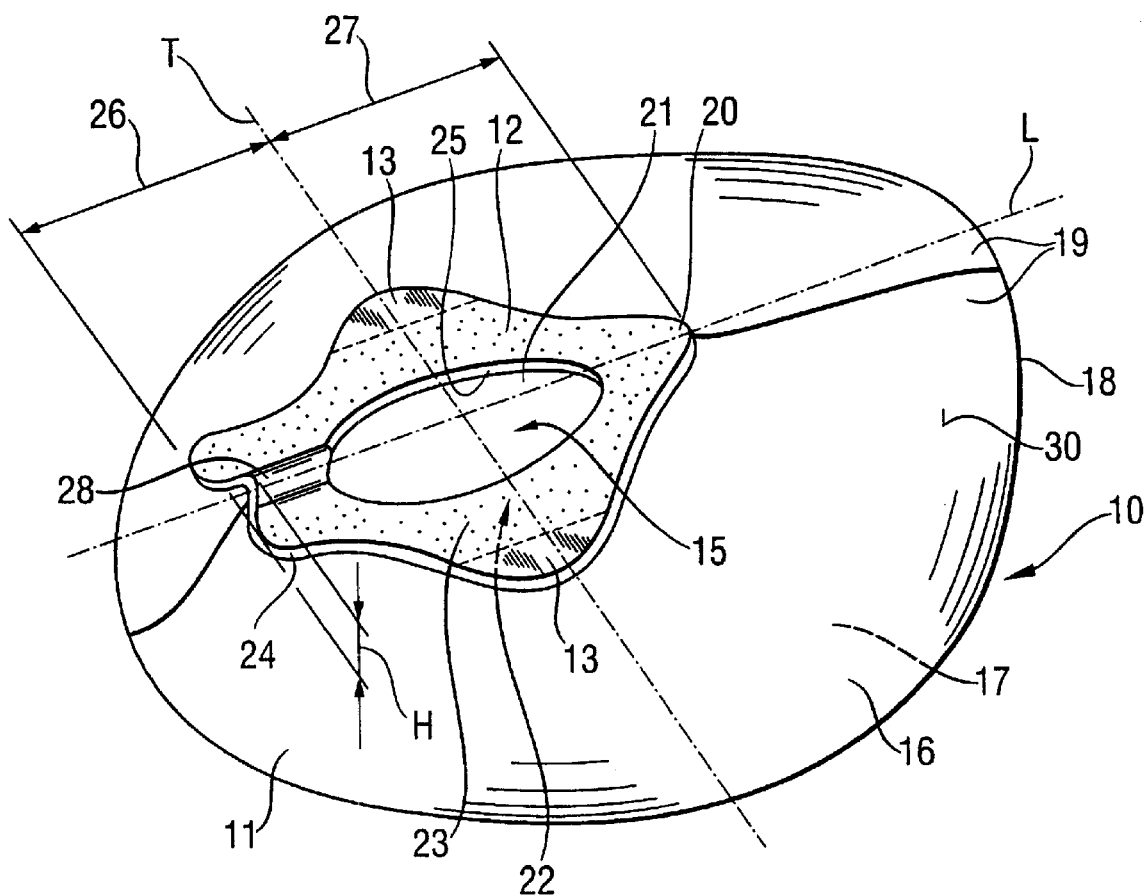
FIG. 1 is a perspective view of a faecal management device according to the present invention.

According to FIG. 1, the faecal management device (10) of the present invention comprises a bag (11) having an aperture and an anatomically-shaped flange (12) surrounding the aperture (21) for adhesive attachment to the skin of the wearer in the anal region in between the buttocks of the wearer and in the gluteal groove.

From FIG. 1, it is evident that the anatomically-shaped flange (12) comprises an outer periphery (24), an inner periphery (25) adjacent to and defining an aperture (21), a longitudinal centerline L and a transverse centerline T orthogonal thereto. The transverse centerline T segments the anatomically shaped flange (12) into a front portion (26) and a rear portion (27). The flange (12) further comprises a wearer facing surface (23) and a garment facing surface (22).

According to the present invention it has been surprisingly found that the presence of a projection positioned on the wearer facing surface of the anatomically shaped flange (12) is particularly effective in reducing and preventing any faecal matter from escaping from the device (10) between the skin and the flange. It is believed that the positioning of such a projection (28) at the front portion (26) of the wearer facing surface of the flange (23) not only provides a flange which more readily conforms to the contours of anatomy of the body, but also provides an improved seal at the positions on the flange, where the exit of faecal matter most readily occurs and thereby prevents any unnecessary contact between the skin and the excreted matter. In addition, a further surprising advantage of the present invention is that the presence of the front projection (28) also assists in the positioning of the device onto the desired skin location of the wearer of the device, further improving the sealing benefit. This is particularly useful for female wearers where the projection may be inserted into the urethra.

According to the present invention the projection is disposed between the outer periphery (24) and the inner periphery (25) of the anatomically-shaped flange (12) in a direction parallel to the longitudinal direction L. In additionthe projection also extends in the transverse direction between the longitudinal side edges on either side of the longitudinal centerline L. More preferably, the flange (12) extends from the outer periphery (24) to the inner periphery (25). In the transverse direction, the projection (28) preferably does not extend across the entire transverse width of the flange but only up to 50% of the width more preferably up to 30% of the width of the flange measured through the center of the projection.

The front projection (28) may be disposed symmetrically or asymmetrically about the longitudinal centerline L. In a more preferred embodiment, the projection (28) is disposed in a substantially symmetrical manner. According to the present invention the projection extends perpendicular to the plane of the flange. It is important that the projection (28) be upstanding and rise above the plane of the flange (12) to an effective height H sufficient to present an abrupt discontinuity to obstruct the movement of the faecal material. As used herein, the term "effective height" refers to the maximum distance in the Z-direction from the garment facing (23) of the flange (12) in its flat orientation of the projection, including adhesive if present on the projection surface. The projection (28) has an effective height ranging from 0.5 millimeters to 15 millimeters. Preferably, the projection (28) has an effective height ranging from 2 millimeters to 10 millimeters, more preferably an effective height of about 3 to 7 millimeters. The effective height measurements are carried out without the aid of a micrometer in order that no pressure is exerted onto the adhesive and flange material. Typically, the projection (28) is orthogonal to the plane of the flange (12). It should be recognized however that if the flange (12) has wrinkles, rugosities, undulations or other deviations from planarity, these should be taken into account at the position of the projection (28), when determining its effective height.

According to the present invention the projection (28) may have any shape. Typically the projection (28) has a longitudinal and/or transverse substantially convex cross section. The front projection (28) is typically independently convex in shape and provides a hump-like or hill-like longitudinal cross section and/or transverse cross section or provides a tubular cross section. The projection may also have a dual hump-like cross section, so as to provide a projection (28) having two or more distinct heights. Preferably, the hump exhibiting the maximum or effective height of the projection will be positioned towards the outer periphery (24) of the flange (12).

The projection (28) is preferably hollow or partially hollow to improve resiliency and flexibility of the projection but may also be completely filled. For embodiments wherein the projection (28) is hollow or partially hollow, the projection may require additional support means in order to maintain the desired resilient configuration of the projection (28). Suitable support means include adhesives or the provision of an elastic material connecting the longitudinal sides of the projection (28) to one another at least the base of the projection (28) on the wearer facing surface (23) of the flange (12).

According to the present invention the projection (28) should preferably be laterally compressible so that the projection will move inward when compressed by lateral forces rather than spring back. The projection (28) should also be resiliently deformable such that if for example the longitudinal sides are compressed the upper or top portion of the projection will be forced upwards and thereby provide a vertical extension of the projection in use and increase the overall effective height of the device. In this manner the sealing effect provided by the projection (28) and more preferably in combination with the flange (12) and adhesive (20) is always maintained, even when the wearer of the device is active during use and thereby places increased pressure onto the device.

The projection (28) configuration may be selected in order to provide further improved fit, for example, if intended for a particular wearer group. For example the front projection (28) for a device intended for female wearers should typically have a greater effective height than the front projection (28) for a device intended for male wearers. However the exact design and dimension can readily be selected by the skilled person in the field.

The projection (28) may be formed as an integral part of the flange or may be provided as separate entities whereby a material which may be different or identical to the flange material is attached to the flange (12) using means known in the art, typically adhesive. Preferably however, the projection (28) is formed as an integral part of the flange. The projection (28) may be made by forming a single pleat in the constituent material of the flange (12) or by thermobonding the flange material. Alternatively, the projection (28) may be provided by a body compatible adhesive material. In a preferred embodiment of the present invention however, the projection (28) is formed from the flange material itself and utilises an adhesive support means.

The projection (28), may either be coated with adhesive or be substantially free from- adhesive. According to a preferred embodiment of the present invention, the projection (28) is also covered with a body-compatible adhesive. For embodiments wherein the projection (28) comprises a dual hump longitudinal cross section for example, it has been found particularly beneficial to provide only one of the surfaces of the hump, preferably the hump providing "the effective height" with a body compatible adhesive. The remaining hump surface may be provided with an anti-slip material such as rubber.

As shown in FIG. 1, the aperture (21) is surrounded by a flange (12) and may be provided in any shape or size, such as circular, oblong, heart shaped and may be symmetrical or asymmetrical, preferably the aperture has an oblong configuration either in the longitudinal or in the transversal direction, most preferably the contours of the aperture are in the shape of two ellipses with the respective main axes being substantially perpendicular.

The flange (12) is attached to the bag (11) according to any means known to the man skilled in the art which may provide permanent or releasable attachment. Preferably however, the flange is attached to the bag by adhesive. Typically, the bag will be attached to the flange, towards the outer periphery of flange so as not to cause any obstruction for the entering faecal matter.

The flange may be provided in any size depending on the wearer group for which the device is intended. Similarly the flange may be provided in any shape and preferably has a symmetrical shape preferably comprising a plurality of lobes (13). The flange comprises a garment facing portion (22) and a wearer facing portion (23).

The flange (12) should be made of soft, flexible and malleable material to allow easy placement of the flange to the perianal area. Typical materials include nonwoven materials, wovens, open celled thermoplastic foams, closed-cell thermoplastic foams, composites of open celled foams and stretch nonwoven, and films, air-laid materials including natural and synthetic fibers, thermally bonded airlaid materials, felt fabrics, needlepunched fabrics, spunlaced fabrics, fluid jet entangled fabrics, wet-laid fabrics, dry-laid fabrics, melt-blown fabrics, staple fibre carding fabrics, spunbonded fabrics, stitch-bonded fabrics, apertured fabrics, combinations of the above or the like. A closed-cell foam of polyethylene has been found effective, but more preferably an open celled polyurethane foam is used. Preferably, such foams have a thickness within the general range of 0.1 to 5 millimeters and a density of 5 to 250 $g/m^2$, more preferably 50 $g/m^2$. Other thermoplastic foam materials, or other suitable plastics sheet materials having the described properties of such foams (i.e., softness, pliability, stretchability, and contractability) might also be used. Preferably, the material of garment facing surface (23) of the flange (12) may extend into the defined aperture (21) area so as to form a skirt or flap of material which prevents unintentional adhesion of the surface edges of the flange defining the aperture to one another during use.

According to the present invention the faecal management device (10) further comprises an attachment means to secure the device to the wearer. Such means include straps and more preferably comprises a body-compatible pressure sensitive adhesive (20) applied to the wearer facing portion (23) of the flange (12).

The adhesive (20) is preferably covered with a release means (not shown) in order to protect the adhesive (20), such as siliconized paper. The adhesive (20) can cover the entire wearer facing surface of the flange or more preferably have at least one, preferably two to six non-adhesive portions. These portions may be adhesive free or may contain inactivated or covered adhesives. As is evident from FIG. 1, the adhesive is in one preferred embodiment not applied to the entire wearer facing surface area of the flange (12), so as to provide lobes (13) on either side of the flange (12) which are non-adhesive and can thereby serve to facilitate placement and removal of the device whilst avoiding contact with the adhesive. These lobes are however preferably also covered by the release means. Before application of the faecal management device (10) to the skin of the wearer, the release means, if present, is removed.

According to the present invention any medically approved water resistant pressure sensitive adhesive may be used to attach the device to the perianal area of the wearer, such as hydrocolloid adhesives and hydrogel adhesives. Particularly effective adhesives in providing the desired adhesive properties to secure the flange to the skin of the wearer at the sensitive perianal area, whilst allowing for relatively painless application and removal are formed from crosslinking polymers with a plastisicer to form a 3-dimensional matrix.

The adhesive (20) can be applied to the wearer facing surface of the flange (12) by any means known in the art such as slot coating, spiral, or bead application or printing. Typically the adhesive is applied at a basis weight of from 20 $g/m^2$ to 2500 $g/m^2$, more preferably from 500 $g/m^2$ to 2000 $g/m^2$ most preferably from 700 $g/m^2$ to 1500 $g/m^2$ depending on the end use envisioned. For example for faecal management devices to be used for babies the amount of adhesive may be less than for faecal management devices designed for active adult incontinence sufferers.

The bag (11) as used herein is a flexible receptacle for the containment of excreted faecal matter. The bag (11) can be provided in any shape or size depending on the intended use thereof, i.e. whether the device is intended for bedridden patients or active patients suffering from incontinence or requiring an artificial bowel or for infants. For example elongated bags which are principally tubular or rectangular are typically utilised by bedridden patients and elderly incontinence sufferers. For more active wearers whether infants or adults, the faecal management device should preferably be anatomically shaped such that the device follows the contours of the body and can be worn inconspicuously by the wearer under normal garments.

Particularly, preferred shapes are flat circular type bags, cone shaped bags, truncated cone shaped bags and pyramidal or truncated pyramidal shaped bags. In a most preferred embodiment of the present invention, the bag (11) has a substantially truncated cone shape. Typically the bags will have a wearer facing portion (16) and a garment facing portion (17). The wearer facing portion (16) of the faecal management device (10) is disposed adjacent the buttocks of the wearer. As such, the wearer facing portion (16) amply covers the buttocks of the wearer and does not hang between the thighs of the wearer.

In addition, the bag (11) is preferably shaped to allow at least partial insertion and retention of the bag in-between the buttocks of the wearer and thereby ensure good contact between the flange and the skin of the wearer. For example the bag (11) may be provided with a neck portion or conduit.

The bag (11) is preferably designed to provide sufficient volume for faecal material under a variety of wearing conditions, also when worn by a freely moving, i.e. not bedridden wearer. Sitting on the bag (11), for example, will result in a largely reduced volume in some areas of the bag. Thus, the bag (11) is preferably shaped to provide sufficient volume in areas which are not subjected to much pressure in wearing conditions such as sitting.

The bag (11) is designed to safely contain any entrapped material, typically it will be liquid impermeable, yet it may be breathable. The bag is designed of sufficient strength to withstand rupture in use, also when pressure on the bag is exerted in typical wearing conditions, such as sitting.

According to the present invention, depending on the shape of the bag (11) required, the bag (11) may be provided from a unitary piece of material or from a number of separate pieces of material, which may be identical or different and which are sealed at their respective peripheries.

In one preferred embodiment the bags herein have a wearer facing portion (16) and a garment facing portion (17) which comprise separate pieces of material. The wearer facing portion (16) and the garment facing portion (17) are sealed at the periphery of the bag (11), thus creating a bag peripheral rim (18). As is visible from FIG. 1, the wearer facing portion (16) of the bag (11) may comprise two further sections (19), which are secured to each other by means known to the man skilled in the art, such as adhesive, thermobonding or pressure bonding in order to provide the desired bag configuration. Said rim (18) may also be inside the bag, thus being coextensive with the inner surface (15) of the bag (11) rather than with the outer surface (30) of the bag (11). Preferably the bag (11) is asymmetrical to the transversal axis, so that the distance measured in the longitudinal direction from the centre of the aperture (21) to the front end of the bag (11) is shorter than the distance measured to the rear end of the bag (11).

According to the present invention the bag (11) can comprise one or multiple layers, preferably two or three layers. The layer on the inside of the bag (11), which will typically at least partially come in contact with faecal material is called the inner layer. The outermost layer of the bag, which will typically at least partially come in contact with the skin to the wearer and the garments of the wearer, is called the outer layer.

The layers of the bag material may be provided from any material, preferably so that the bag is liquid impervious. The layers may in particular comprise any material such as non-wovens or films. In a preferred embodiment of the present invention a laminate may be formed from a non-woven layer and a film. The laminate can be formed by means known to the man skilled in the art.

Any non-woven layer can comprise felt fabrics, spunlaced fabrics, fluid jet entangled fabrics, air-laid fabrics, wet-laid fabrics, dry-laid fabrics, melt-blown fabrics, staple fibre carding fabrics, spunbonded fabrics, stitch-bonded fabrics, apertured fabrics, combinations of the above or the like.

Suitable film materials for any of said layers preferably comprise a thermoplastic material. The thermoplastic material can be selected from among all types of hot-melt adhesives, polyolefins especially polyethylene, polypropylene, amorphous polyolefins, and the like; material containing meltable components comprising fibers or polymeric binders including natural fibers such as cellulose-wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapor permeable materials including microporous films such as those supplied by EXXON Chemical Co., Ill., U.S. under the designation EXXAIRE or those supplied by Mitsui Toatsu Co., Japan under the designation ESPOIR NO; and monolithic breathable materials such as Hytrel™ available from DuPont and Pebax™ available from ELF Atochem, France.

In a preferred embodiment a film, which is comprised in any layer, is preferably permeable to gases such as air and to vapor such as water vapor in order to avoid the problem of entrapment and condensation of moisture vapor given off by the body of the wearer and thus, the hot, clammy and uncomfortable conditions after a short period of use.

The outer layer of the bag is preferably provided with a non-woven layer. Such material layers present an uneven surface to the skin of the wearer and thus reduce significantly the problem of occlusion and greatly improve skin healthiness.

In one preferred embodiment of the present invention, the bag comprises two layers. Preferably the outer layer comprises a non-woven layer and the inner layer comprises a film.

In yet another preferred embodiment of the present invention, the bag (11) comprises three layers, preferably one film and two non-woven layers. In an even more preferable embodiment the film is interposed between the two non-woven layers. This sequence of layers results in a closed fibrous structure, which has a particularly pleasing sensation on contact with the skin of the wearer. In yet another preferred embodiment the inner layer comprises a film and the other two layers comprise non-wovens.

The non-woven layer or the non-woven layers comprised by the bag (11) may be hydrophobic or hydrophilic. If the bag (11) does not comprise a film layer, preferably at least one non-woven layer is hydrophobic. As a consequence, fluid penetration is resisted through the wearer facing portion (16) and the garment facing portion (17) of the faecal management device (10). If the bag comprises a film or a hydrophobic non-woven layer, further non-woven layers may be hydrophilic.

Typically, the non-woven layer is treated with a surface active material, such as a fluorochemical or other hydrophobic finishings, to provide the requisite hydrophobicity. The non-woven layer, however, may equally be treated with coatings of liquid impervious materials such as hot-melt adhesives or coatings of silicone or other hydrophobic compounds such as rubbers and vegetable and mineral waxes or it may be physically treated using nano-particulates or plasma coating techniques, for example.

The non-woven layer can also be treated with agents to improve the tactile perceivable softness of the wearer facing portion (16) and the garment facing portion (17). The agents include but are not limited to vegetable, animal or synthetic oils, silicone oils and the like. The presence of these agents are known to impart a silky or flannel-like feel to the non-woven layer without rendering it greasy or oily to the tactile sense of the wearer. Additionally, surfactant material, including anionic, non-anionic, cationic and non-cationic surfactants, may be added to further enhance softness and surface smoothness.

Furthermore, the non-woven layer may be impregnated with a lotion to provide desirable therapeutic or protective coating lotion benefits. The lotion coating on the wearer facing portion (16) and the garment facing portion (17) is transferable to the skin of the wearer by normal contact and wearer motion and/or body heat. Generally, mineral oil in the form of a lotion is recognised as being effective in imparting a soothing, protective coating to the skin of the wearer. It is also possible to impregnate the non-woven layer with a solid oil phase of cream formulation or to incorporate into the non-woven layer an array of pressure- or thermal- or hydrorupturable capsules containing for example, baby oil.

In one embodiment of the present invention the bag may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including conform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The absorbent material may be positioned in the bag (11) in any suitable manner. For example, the absorbent material may be loosely arranged within the bag or may be secured to the inner layer of the bag (11). Any known techniques for securing absorbent material to nonwoven and film substrates may be used to secure the absorbent material to the inner layer of the bag. The absorbent material may also be arranged to have any desired shape or configuration (e.g., rectangular, oval, circular, etc.).

Figure 2:
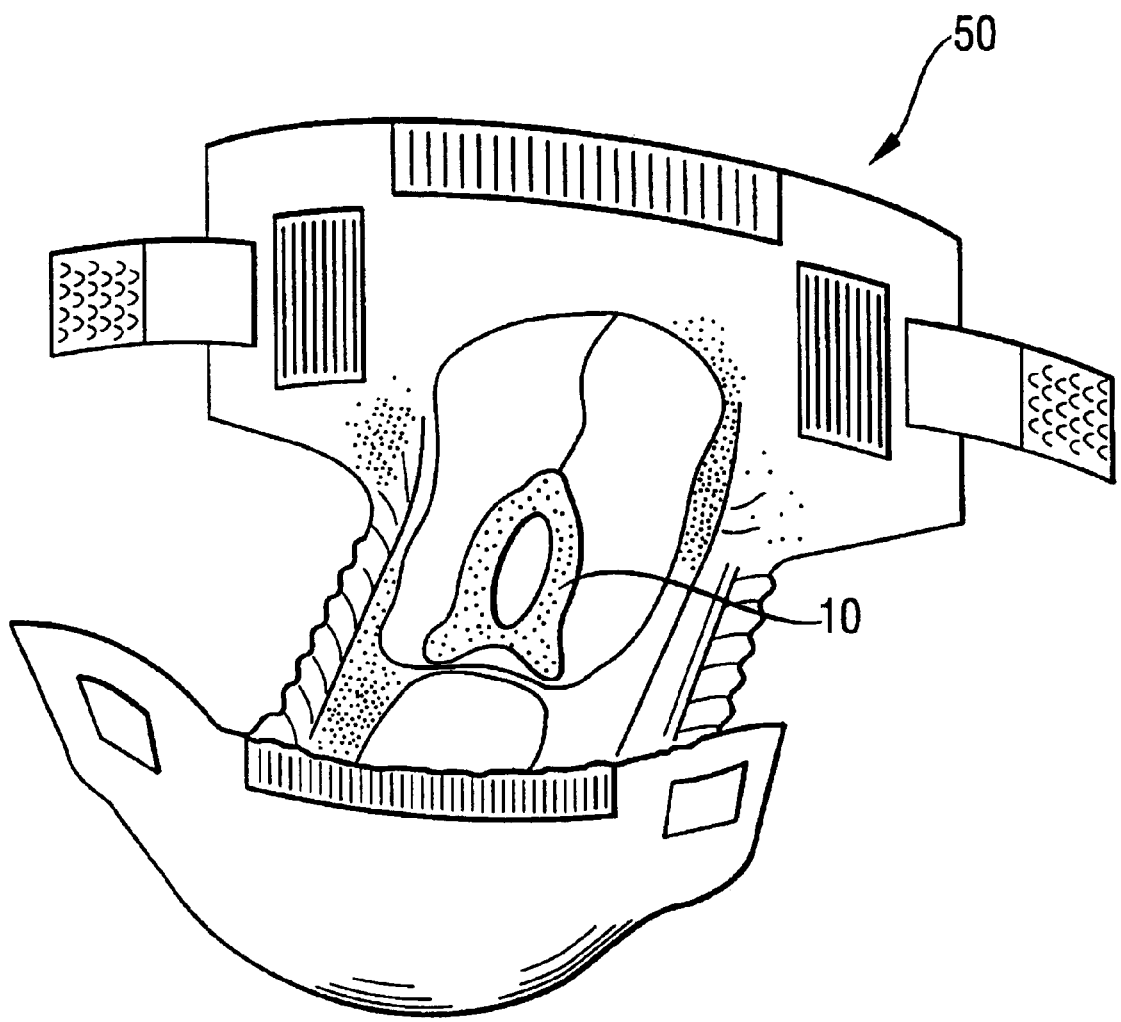
FIG. 2 shows a perspective view of the faecal management device in conjunction with a disposable diaper.

Detailed Description of a Diaper to be Worn in Combination with the Faecal Management Device The faecal management device (10) of the present invention has been found to be particularly useful and beneficial when used in conjunction with a garment, or diaper (50), preferably a disposable diaper—refer to FIG. 2. The faecal management device (10) is preferably first positioned in the perianal area of the wearer before the disposable diaper (50) is applied. In particular, the diaper (50) is positioned over the faecal management device (10) and fastened in a conventional manner around the body of the wearer. It has been found that, in addition, to providing excellent separation between urine and faecal material, the combined faecal management device (10) and diaper (50) system actually reduces skin irritation, which may at times occur, especially since the group of typical wearers includes the very old, the very young and the unhealthy wearers. In effect, the presence of the faecal management device (10) permits the formation of a separation layer between the skin of the wearer and the diaper (50), i.e. a part of the absorbent core (58) of the diaper (10). The diaper (50) can be of the conventional type (an embodiment of which is described below although not a limiting example by any means) or can be adapted to contain in an effective and comfortable manner the faecal management device (10) according to the teachings of the present invention.

As used herein, the term "disposable diapers" refers to articles which absorb and contain body extrudates; and more specifically, refers to articles which are placed against or in proximity to the body of the wearer to absorb and contain the various extrudates discharged from the body and which are intended to be discarded after a single use (i.e., they are not intended to be laundered or otherwise restored or reused) and, preferably, to be recycled, composted or otherwise disposed of in an environmentally compatible manner. As used herein, the term "diaper" refers to a garment generally worn by infants or incontinence sufferers that is drawn up between the legs and fastened about the waist of the wearer.

Figure 3:
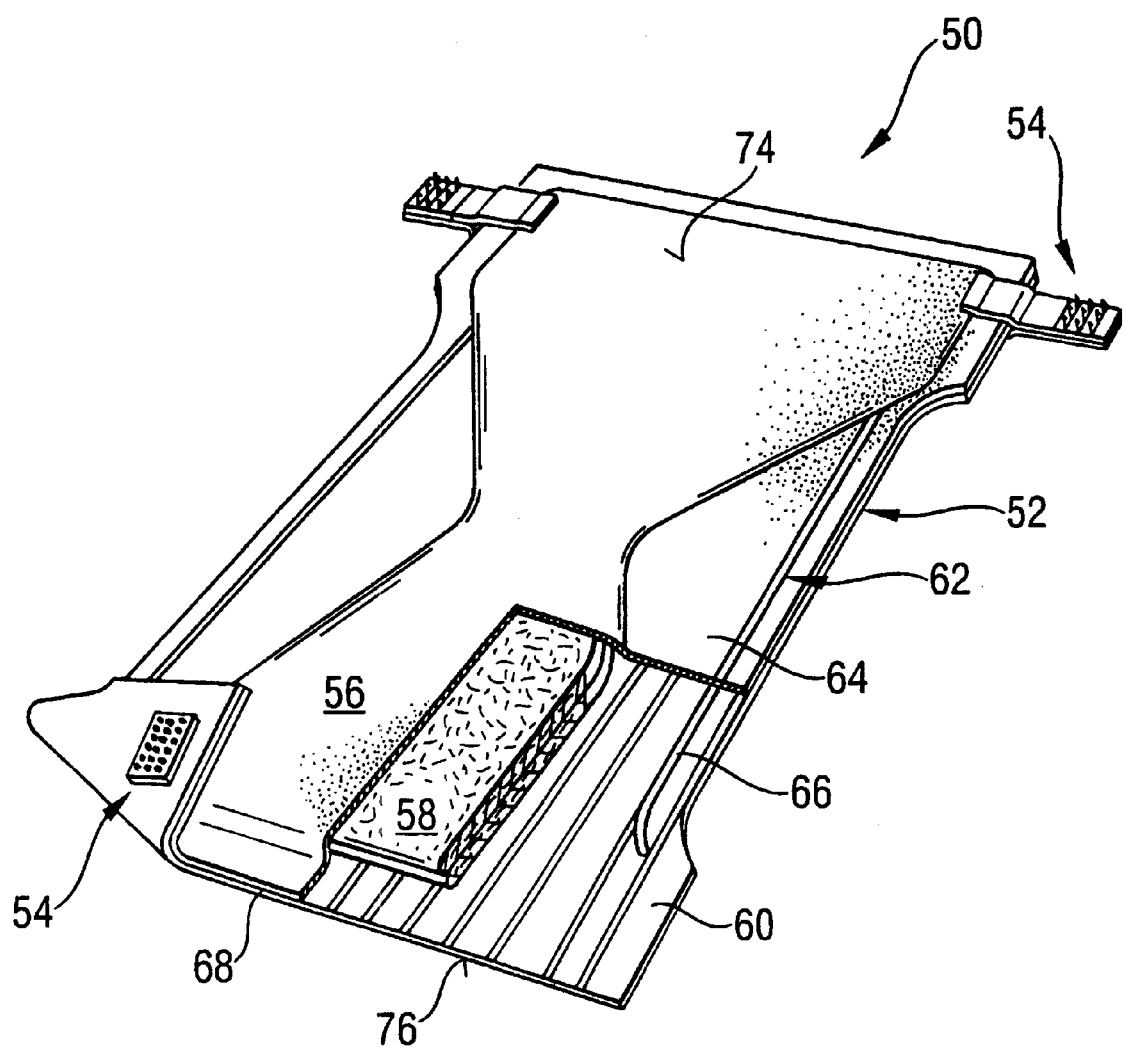
FIG. 3 is a partially cut-away perspective view of a disposable diaper embodying the present invention.

FIG. 3 is a partially cut-away perspective view of a diaper (50) embodying the present invention prior to it being placed on the wearer over the faecal management device (10). As is visible from FIG. 3, a preferred diaper (50) comprises a body portion (52) and a refastenable mechanical fastening device (54). A preferred body portion (52) comprises a liquid pervious topsheet (56), and absorbent core (58), a liquid impervious backsheet (60), and elastically contractible leg cuffs (62); each leg cuff (62) preferably comprising a side flap (64) and one or more elastic members (66). For simplicity purposes, only one elastic member (66) is shown in the side flap (64). While the topsheet (56), the absorbent core (58), the backsheet (60), the side flaps (64), and the elastic members (66) may be assembled in a variety of well-known configurations. A preferred disposable diaper configuration is shown and generally described in U.S. Pat. No. 3,860,003, an even more preferred disposable diaper configuration is shown and generally described in WO 93/16669. In this preferred diaper configuration, the backsheet (60) is joined to the topsheet (56); the absorbent core (58) is positioned between the topsheet (56) and the backsheet (60); the side flaps (64) extend outwardly from and along each side edge of the absorbent core (58); and the elastic member (66) is operatively associated with each side flap (64).

FIG. 3 shows the body portion (52) in which the topsheet (56) and the backsheet (60) are coextensive and have length and width dimensions generally larger than those of the absorbent core (58). The topsheet (56) is superposed on the backsheet (60) thereby forming the periphery (68) of the body portion (52).

The body portion (52) has an inside surface (74) and an outside surface (76). When a backsheet (60) is used, it typically forms the outside surface (76) of the body portion (52). The inside surface (74) is that surface of the diaper (50) opposite the outside surface (76) and in the embodiment shown is typically formed by the topsheet (56). In general, the inside surface (74) of the diaper (50) is that surface coextensive with the outside surface (76) and which is for the greater part in contact with the wearer when the diaper (50) is worn.

The absorbent core (58) of the body portion (52) may be any absorbent means which is generally compressible, conformable, non-irritating to the skin of the wearer, and capable of absorbing and retaining liquids such as urine and other certain bodily discharges. The absorbent core (58) may be manufactured in a variety of sizes and shapes (for example, rectangular, hour-glass, "T" shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including conform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core (58) may also be varied (for example, the absorbent core (58) may have varying caliper zones, hydrophilic gradients, superabsorbent gradients, or lower average density and lower average basis weight acquisition zones; or may comprise one or more layers or structures). Further, the size and absorbent capacity of the absorbent core (58) may be varied to accommodate wearers ranging from infants to adults.

The backsheet (60) is impervious to liquids (for example, urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (60) prevents the exudates absorbed and contained in the absorbent core (58) from soiling articles which are in contact with the diaper (50) such as undergarments and bedding. The backsheet (60) may thus comprise polymeric films such as thermoplastic films of polyethylene or polypropylene, or composite materials such as film-coated non-woven material. Exemplary films are manufactured by Tredegar Industries, Inc. of Terre Haute, Ind., USA or BP-Chemical PlasTec, Rotbuchenstrasse 1, D-8000 München, Germany.

The backsheet (60) is preferably textured to provide a more clothlike appearance. Further, the backsheet (60) may also permit vapors to escape from the absorbent core (58) while still preventing exudates from passing through the backsheet (60) by, for example, being supplied with microapertures. The size of the backsheet (60) is dictated by the size of the absorbent core (58) and the exact diaper design selected.

The topsheet (56) of the diaper is compliant, soft feeling and non-irritating to the skin of the wearer. Further, the topsheet (56) is liquid pervious permitting liquids (for example, urine) to readily penetrate through its thickness. A suitable topsheet (56) may be manufactured from a wide range of materials, such as porous foams, reticulated foams, apertured films; or woven or non-woven webs of natural fibers (for example, wood or cotton fibers) or from a combination of natural and synthetic fibers. Preferably, it is made of a material that isolates the skin of the wearer from liquids retained in the absorbent core (58).

There are a number of manufacturing techniques which may be used to manufacture the topsheet (56). For example, the topsheet (56) may be a nonwoven web of fibers. An exemplary topsheet (56) is carded and thermally bonded by means well-known to those skilled in the fabric art. A suitable topsheet (56) is manufactured by, for example, Veratec Inc., a division of International Paper Company, of Walpole, Mass., USA. A topsheet (56) particularly preferred for incontinence garments comprises a formed thermoplastic film.

What is claimed is:

1. A faecal management device comprising a bag, said bag having an aperture and a flange at least partially surrounding said aperture and being attached to said bag, said flange having an inner periphery and an outer periphery adjacent said aperture, said flange further comprising a projection extending outwardly from said flange to a height, said projection comprising a resiliently deformable foam material having a thickness of 0.1 to 5 millimeters, whereby said height of said projection may be increased in response to lateral compression of said projection.

2. A device according to claim 1 wherein said projection comprises open cell foam material.

3. A device according to claim 1 wherein said projection is hollow.

4. A faecal management device comprising a bag, said bag having an aperture and a flange at least partially surrounding said aperture and being attached to said bag, said flange having an inner periphery and an outer periphery adjacent said aperture, said flange further comprising a projection extending outwardly from said flange to a height, said projection comprising a resiliently deformable material, whereby said height of said projection may be increased in response to lateral compression of said wherein said projection extends to two different heights, a first height and a second height distinct therefrom, said first height being oriented towards said outer periphery of said flange, said second height being oriented towards said inner periphery of said flange.

5. A device according to claim 4 wherein said first height is greater than said second height.

6. A device according to claim 5 wherein at least one of said first height and said second height ranges from 0.5 to 15 millimeters.

7. A device according to claim 6 wherein at least one of said first height and said second height ranges from 2 to 10 millimeters.

* * * * *